United States Patent
Imberdis et al.

(10) Patent No.: US 11,591,225 B2
(45) Date of Patent: Feb. 28, 2023

(54) METHOD FOR PRODUCING CARBON MONOXIDE

(71) Applicant: COMMISSARIAT A L'ENERGIE ATOMIQUE ET AUX ENERGIES ALTERNATIVES, Paris (FR)

(72) Inventors: Arnaud Imberdis, Paris (FR); Thibault Cantat, Issy les Moulineaux (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 45 days.

(21) Appl. No.: 16/963,190

(22) PCT Filed: Jan. 14, 2019

(86) PCT No.: PCT/EP2019/050838
§ 371 (c)(1),
(2) Date: Jul. 17, 2020

(87) PCT Pub. No.: WO2019/141634
PCT Pub. Date: Jul. 25, 2019

(65) Prior Publication Data
US 2021/0188650 A1  Jun. 24, 2021

(30) Foreign Application Priority Data
Jan. 17, 2018  (FR) ..................... 1850366

(51) Int. Cl.
| | | |
|---|---|---|
| *C01B 32/40* | (2017.01) | |
| *B01J 31/02* | (2006.01) | |
| *B01J 31/06* | (2006.01) | |
| *B01J 35/12* | (2006.01) | |
| *C07C 1/04* | (2006.01) | |
| *C07C 29/151* | (2006.01) | |
| *C07C 45/50* | (2006.01) | |
| *C07C 51/12* | (2006.01) | |
| *C07C 67/08* | (2006.01) | |

(52) U.S. Cl.
CPC .......... *C01B 32/40* (2017.08); *B01J 31/0212* (2013.01); *B01J 31/0239* (2013.01); *B01J 31/0252* (2013.01); *B01J 31/06* (2013.01); *B01J 35/12* (2013.01); *C07C 1/0485* (2013.01); *C07C 29/1518* (2013.01); *C07C 45/50* (2013.01); *C07C 51/12* (2013.01); *C07C 67/08* (2013.01); *B01J 2231/005* (2013.01); *B01J 2531/002* (2013.01)

(58) Field of Classification Search
CPC ... C01B 32/40; C07C 1/0485; C07C 29/1518; C07C 45/50; C07C 51/12; C07C 67/08; B01J 31/0212; B01J 31/0239; B01J 31/0252; B01J 35/12
See application file for complete search history.

(56) References Cited

U.S. PATENT DOCUMENTS

| | | | |
|---|---|---|---|
| 3,716,619 A | 2/1973 | Lynn et al. | |
| 4,474,744 A * | 10/1984 | Green | ..................... C07C 29/00 |
| | | | 568/876 |

FOREIGN PATENT DOCUMENTS

| | | |
|---|---|---|
| FR | 2 058 060 A5 | 5/1971 |
| FR | 3 043 401 A1 | 5/2017 |

OTHER PUBLICATIONS

Hideji et al., method of producing carbon monoxide, (JP 2002114509A machine translation), Sep. 29, 2000.*
Carpentier, J.-F., et al., "A Novel and Convenient Method for Palladium-Catalysed Alkoxycarbonylation of Aryl and Vinyl Halides Using HCO2R / NaOR System," Tetrahedron Letters 32(36):4705-4708, 1991.
International Search Report dated Mar. 27, 2019, issued in corresponding International Application No. PCT/EP2019/050838, filed Jan. 14, 2019, 14 pages.
Written Opinion issued in corresponding International Application No. PCT/EP2019/050838, filed Jan. 14, 2019, 13 pages.

* cited by examiner

*Primary Examiner* — Jafar F Parsa
(74) *Attorney, Agent, or Firm* — Christensen O'Connor Johnson Kindness PLLC (57) ABSTRACT

The present invention concerns a method of production for carbon monoxide using a derivative of formic acid, in particular an alkyl formate.
It also concerns a method chosen from among, the method of production of methanol, the method of production of acetic acid (Monsanto and Cativa methods), the method of hydroformylation of olefins (oxo and aldox method), the method of production of hydrocarbons (Fischer-Tropsch method), or the method of carbonylation of nickel (Mond method), comprising a step of production of carbon monoxide using an alkyl formate of formula (I) by the method according to the invention.
It further concerns a "CO pump" or "CO liquid storage" method comprising a step of production of carbon monoxide using an alkyl formate of formula (I) according to the method of the invention.

17 Claims, 2 Drawing Sheets

PS = radical polystyrène

Figure 4

METHOD FOR PRODUCING CARBON MONOXIDE

The present invention concerns a method of production for carbon monoxide making use of a derivative of formic acid, in particular an alkyl formate.

It also concerns a method chosen from among, the method of production of methanol, the method of production of acetic acid (Monsanto and Cativa methods), the method of hydroformylation of olefins (oxo and aldox method, the method of production of hydrocarbons (Fischer-Tropsch method), or the method of carbonylation of nickel (Mond method), comprising a step of production of carbon monoxide making use of an alkyl formate of formula (I) by the method according to the invention.

It concerns, furthermore, a "CO pump" or "CO liquid storage" method comprising a step of production of carbon monoxide making use of an alkyl formate of formula (I) according to the method of the invention.

Today the petrochemical industries supply fuels, plastics, medicines, etc. Fossil fuels thus represent more than 85% of world energy production whereas organic chemical consumables (plastics, fertilizers, textiles . . . ) come at 95% from the use of oil and natural gas. The challenge is to develop efficient catalysts for recycling $CO_2$ and biomass waste.

CO would be an intermediary, source of carbon convenient for meeting this challenge, the latter having been for example used by Germany during the second world war to produce liquid fuels by the Fisher-Tropsch method.

Industrial Scale Production of CO

On the industrial scale, several ways of producing carbon monoxide are known.

Carbon monoxide can be produced by partial oxidation of gaseous hydrocarbons coming from natural gas or by the gasification of coal or coke. As such, the Shell method or the Texaco method can be mentioned. These methods use high temperatures (1100-1500° C.) as well as high pressures (60-80 bar) leading to the obtention of a gas mixture, requiring purification for the production of a pure gas. Moreover, multiple secondary reactions occur due to the high temperatures (Gaurav Nahar, Valerie Dupont: Hydrogen production from simple alkanes and oxygenated hydrocarbons over ceria-zirconia supported catalysts: Review. Renewable and Sustainable Energy Reviews. Band 32, 2014, S. 777-796, doi:10.1016/j.rser.2013.12.040).

The reverse water gas shift reaction (rWGSR) is another way of producing CO on an industrial scale.

In the presence of an appropriate catalyst, the reaction takes place according to the following equation:

$CO_2+H_2 \rightarrow CO+H_2O$ ($\Delta H$=+41.2 kJ/mol at 298K; $\Delta G$=+28.53 kJ/mol at 298K)

This reaction is thermodynamically unfavourable and has a low equilibrium constant even at temperatures of 400° C. Also, to obtain satisfactory conversion rates, either the reactor has to be fed with a $CO_2/H_2$ mixture rich in hydrogen, or rich in carbon dioxide (which means that the excess hydrogen or carbon dioxide has to be captured from the exhaust gases with a filtering membrane and returned into the reactor), or the operating temperature of the reactor has to be increased (the equilibrium constant is 0.5 only at 750° C. requiring hard temperature conditions). The choice of the catalyst will then depend on this operating temperature. According to the experiments carried out by Pioneer Astronautics in Lakewood, Colo., the best catalyst at low temperature for this reaction is a mixture of copper and nickel supported on silica. This catalyst is exclusively selective for CO (i.e. it produces only carbon monoxide) with 60% conversion of $CO_2$ into CO, at 350° C., 150 torr, and a $CO_2/H_2$ reactor feed ratio of ¼ (Whitlow, Jonathan E.; Parish (2003). "Operation, Modeling and Analysis of the Reverse Water Gas Shift Process". doi:10.1063/1.1541409). The Camere method uses ZnO—Al catalysts at 600° C. or ZnO—Cr catalysts for temperatures higher than 600° C. (Park, S.-W., Joo, O.-S., Jung, K.-D., Kim, H., & Han, S.-H., 2000, Korean Journal of Chemical Engineering, 17(6), 719-722. https://doi.org/10.1007/BF02699123).

Another way to produce CO is the electrochemical reduction of $CO_2$ into CO.

The electrochemical reduction of $CO_2$ consists in having $CO_2$ react with several electrons and protons to produce synthesis hydrocarbons and oxygenated compounds. Two technologies can be mentioned:

High temperature electrolysis: co-electrolysis of $CO_2$ and water. Water and $CO_2$ are co-electrolysed at high temperature (700-800° C.) to produce syngas ($CO+H_2$) which results, by catalytic reaction, in hydrocarbons or in alcohols. This system uses both electrical energy and heat to reduce the $CO_2$ molecule.

Ambient temperature electrolysis (20 to 25° C.) in electro-catalytic cells. In this reaction, electrons are supplied by electrical energy, generally from solar panels or other renewable energies, and hydrogen ions by a chemical element (e.g. HCl) or gaseous hydrogen directly.

Both these electrolysis technologies present several disadvantages.

1) slow reaction kinetics: this leads to an overvoltage >1.0 V, which considerably increases the energy cost for the electrolysis process;

2) low selectivity of $CO_2$ reduction: $CO_2$ reduction and hydrogen production are two competing reactions; hydrogen is very often a by-product accompanying $CO_2$ reduction when electrochemical reduction is carried out in water;

3) formation of various by-products: they are mainly in electrolytic solution and the separation and recovery of the reaction by-products polluting the electrolytic solution represent high energy costs;

4) deactivation: the electrode's catalyst loses its great initial selectivity and its reactivity after a short time of operation;

5) low tolerance to the impurities and to contamination: surface contamination and non-pure electrolyte due to the reaction by-products often result in low productivity and selectivity of the hydrocarbon products.

A major industrial source of CO is the "producer gas", which results from the combustion of coal at high temperature. It can be obtained, for example, in a furnace, wherein air passes through a coalbed. The initially produced $CO_2$ balances with the remaining hot coal to give CO. The reaction of $CO_2$ with coal to give CO is described as the Boudouard reaction.

$CO_2+C \rightarrow 2\ CO$ ($\Delta H$=170 kJ/mol)

Above 800° C., CO is the predominant product.

Another industrial source of CO is the "steam activation of carbon" method, which is an endothermic reaction between steam and carbon at around 1000° C.:

$H_2O+C \rightarrow H_2+CO$ ($\Delta H$=+131 kJ/mol)

Carbon monoxide is also produced industrially by the direct oxidation of carbon by a limited addition of oxygen or air at 200° C.

$$2C_{(s)}+O_2 \rightarrow 2CO_{(g)}$$

The reduction process can be favoured by heating, by exploiting the positive entropy of the reaction. The Ellingham diagram shows that CO formation is favoured compared to $CO_2$ at high temperature.

It may also be noted that carbon monoxide is produced in the blast furnaces of steel mills.

Laboratory Scale Production of CO

1) Production of Gaseous CO:

By Stoichiometric Reaction

Carbon monoxide can be produced by the dehydration of formic acid with concentrated sulphuric acid. The reaction is stoichiometric and uses a strong concentrated acid (Ernest R. Schierz J. Am. Chem. Soc., 1923, 45 (2), pp 447-455 DOI: 10.1021/ja01655a021).

A homogeneous mixture of powdered zinc and calcium carbonate heated to 90° C. releases CO and leaves behind zinc oxide and calcium oxide.

$$Zn+CaCO_3 \rightarrow ZnO+CaO+CO$$

Methane iodide and silver nitrate can react in water to form CO.

$$CHI_3+3AgNO_3+H_2O \rightarrow 3HNO_3+CO+3AgI$$

Metal oxalate salts release CO when they are heated, leaving carbonate as the by-product:

$$Na_2C_2O_4 \rightarrow Na_2CO_3+CO$$

In 2012, Manabe uses trichlorophenyl formate as CO equivalent in-situ in carbonylation reactions in the presence of a complex of is palladium and an equivalent of base. He also demonstrates that trichlorophenyl formate releases CO in the presence of an equivalent of triethylamine in chloroform at ambient temperature (Ueda T, Konishi H, Manabe K, Organic Letters, 2012, vol: 14 (20), pp: 5370-5373).

Disadvantages: Use of an equivalent base for decarbonylation and a percentage of CO in the molecule of 12.6% low compared with methyl formate for example (46.7%).

In 2015, Fleischer describes an equivalent of CO recyclable from a carefully chosen amine and using a formylation reaction in the presence of $CO_2$. CO is released at ambient temperature in DMF in the presence of a base in stoichiometric quantity, in general, a carbonate (Gehrtz P, Hirschbeck V, Fleischer I, Chem. Commun., 2015, vol: 51 (63), pp: 12574-12577).

Disadvantages: Use of an equivalent base for decarbonylation and a percentage of CO in the molecule of 13.3% low compared with methyl formate for example (46.7%).

By Catalytic Reaction

Carbon monoxide can be produced by the decarbonylation of alkyl formates by a metal catalyst (copper, ruthenium, rhodium, osmium), like the methods of Doyle in 1981, Alper in 1987, Leismann in 1989, and Mortreux in 1992. In these methods the temperatures are higher than 100° C. (Doyle G, Exxon Research and Engineering Co., 1981, pp: 1-4); Zahalka H, Alper H, Tetrahedron Letters, 1987, vol: 28 (20), pp: 2215-2216).

Disadvantages: Use of metals for the decarbonylation as well as the temperature of around 100° C.

Carbon monoxide can be produced by the decarbonylation of alkyl formates with an organic catalyst. This is described in a patent of 1984 with guanidines with reaction temperatures between 140° C. and 150° C. in the absence of solvent (EP0115387B1, 1984 pp: 1-4).

Disadvantage: Use of high temperatures of around 140° C. for the decarbonylation.

Carbon monoxide can again be produced with amines and phosphines as catalyst at 190° C. without solvent, as published by Abbayes, in 1993 (Vega F, Clément J, des Abbayes H, Tetrahedron Letters, 1993, vol: 34 (50), pp: 8117-8118).

Disadvantage: Use of high temperatures of around 190° C. for the decarbonylation.

Skrydstrup develops from 2016 (Friis S, Lindhardt A, Skrydstrup T, Accounts of Chemical Research, 2016, vol: 49 (4), pp: 594-605), CO precursors, now marketed, which release carbon monoxide by the addition of catalyst based on palladium or potassium fluoride.

-continued

Disadvantages: Use of a rare metal and ligands (costly) for the decarbonylation in the first case and use of a source of stoichiometric fluoride which remains toxic even if lethal doses are in the order of a gram. Moreover a percentage of CO in the molecule of 13.5% in the first substitute and 9.2% in the second. Both these percentages are low compared with methyl formate for example (46.7%).

2) Passage by the Formation of CO In-Situ: Decarbonylation Occurs in Tandem with the Reaction which Consumes Carbon Monoxide In 1991, Mortreux proposes using the alkyl formate system, sodium alcoholate in the presence of palladium in DCM so as to use the formate as carbonylation agent of alkyl halides. He uses 1.4 equivalent of alcoholate and heats at minimum to 40° C. in the presence of palladium (Carpentier J, Castanet Y, Brocard J, Mortreux A, Petit F, Tetrahedron Letters, 1991, vol: 32 (36), pp: 4705-4708).

In 2016, Wu uses an aromatic triformate (TFBen) synthesised from formic acid which is used in-situ in the presence of a complex of palladium and triethylamine at 100° C. to carbonylate an aryl halide (Jiang L, Qi X, Wu X, Tetrahedron Letters, 2016, vol: 57 (30), pp: 3368-3370).

Disadvantages: The balance of the decarbonylation is displaced by a successive reaction, which consumes CO and is not isolated (which does not allow "autonomous" decarbonylation to be shown).

The widespread and simple use of these systems apart from the examples of these publications is not enabled because it is conditioned by the nature of the tandem reaction.

Industrial Scale Production of Methyl Formate

Methyl formate is produced industrially by the carbonylation of methanol by carbon monoxide in the presence of a strong base, such as sodium methanoate (U.S. Pat. No. 4,216,339):

This method, commercially used by BASF for example, gives a selectivity of 96% compared with methyl formate. The catalyst of this method is sensitive to water, which can be present in carbon monoxide, which is currently derived from the synthesis gas. The carbon monoxide must be imperatively dry.

The state of the art given in Sections 1) and 2), thus indicates a real need for a carbon monoxide (CO) production method that is efficient, technically and economically viable and which uses a sustainable source of carbon monoxide (CO).

There is also a real need for a method of producing carbon monoxide (CO) that is efficient and that does not require demanding operating conditions, especially high temperatures.

There is also a real need for a method of producing carbon monoxide (CO) that uses a liquid source rich in CO (percentage of CO transported by the source greater than 20%).

There is, moreover, a real need for a method of producing carbon monoxide (CO) as described above which involves an efficient catalyst (capable of increasing the rate of conversion of the carbon source in CO), inexpensive and/or slightly toxic compared with known catalysts in the sense that it does not contain:

alkaline earth metals of Group IIA of the Periodic Table of the Elements (such as magnesium and calcium);

metals of Group IIIA, i.e. aluminium, gallium, indium and thallium;

transition metals of Group IB to VIIIB of the Periodic Table of the Elements (such as nickel, iron, cobalt, zinc, copper, rhodium, ruthenium, platinum, palladium, iridium);

rare earths whose atomic number are comprised between 57 and 71 (such as lanthanum, cerium, praseodymium, neodymium); or actinides whose atomic number are comprised between 89 and 103 (such as thorium, uranium).

The precise aim of the present invention is to respond to these needs by providing a method of production of carbon monoxide (CO) wherein an alkyl formate of formula (I)

$$H-COOR \tag{I}$$

where R is an alkyl comprising 1 to 12 carbon atoms, is put into contact with a catalyst, said method being characterized in that the catalyst is chosen from among:

alcoholates having a pKa>15 in water, or a pKa>27 in acetonitrile or DMSO; or nitrogenous bases having a pKa>15 in water, or a pKa>27 in acetonitrile or DMSO; and in that the putting into contact is carried out in a or in a mixture of at least two polar and aprotic solvents, at a temperature less than 35° C., preferably at a temperature less than or equal to 30° C.

The use of an alkyl formate of formula (I) in this method makes it possible to use liquid storage means, rich in CO and sustainable source of carbon monoxide (CO). Finding efficient catalysts for the conversion of alkyl formate to CO that are inexpensive and/or low in toxicity and which allow mild conversion (temperature <35° C., preferably temperature 30° C.) has been found to be quite a technical challenge.

The method of the invention can constitute an interesting alternative to the traditional methods of obtaining CO, such as for example partial oxidation of hydrocarbons, reverse water gas shift reaction (rWGSR), coal combustion, stoichiometric reaction of formic acid with sulphuric acid or the various chemical reactions involving restrictive reaction conditions.

The method of the invention uses a catalytic system (catalytic charge from 0.1 to 10%) and a percentage of CO in the molecule of 46.7% when methyl formate is used (37.8% for ethyl formate, 31.8% for n-propyl formate, 27.5% for tert-butyl formate) much higher than other existing CO substitutes other than methyl formate. The percentage of CO in the molecule is referred to when the molecule considered as a CO equivalent is analysed to determine the percentage share that CO (of molar mass 28 g/mol) represents in the molar mass M of the molecule.

The method of the invention releases gaseous CO that can easily be used in various processes using gaseous CO.

The method of the invention makes it possible to produce carbon monoxide with a catalyst forming part of the family of strong bases (pKa>15 in water; or pKa>27 in acetonitrile or DMSO) and easily accessible. The use of catalysts based on rare or costly metals or again comprising costly ligands is no longer necessary. Moreover, with the method of the invention, the use of a toxic catalyst such as, for example, a fluoride source is avoided.

Thus, the catalysts used in the method of the invention present the advantage of overcoming the toxicity problems generally observed for metal catalysts as well as cost problems associated with the use of precious metals.

Indeed, in the method of the invention, the catalyst used does not contain:
- alkaline earth metals of Group IIA of the Periodic Table of the Elements chosen from among magnesium and calcium;
- metals of Group IIIA, chosen from among aluminium, gallium, indium and thallium.
- transition metals of Group IB to VIIIB of the Periodic Table of the Elements chosen from among nickel, iron, cobalt, zinc, copper, rhodium, ruthenium, platinum, palladium and iridium;
- rare earths whose atomic number is comprised between 57 and 71 chosen from among lanthanum, cerium, praseodymium and neodymium; or
- actinides whose atomic number is comprised between 89 and 103 chosen from among thorium and uranium.

By catalyst, for the purpose of the invention, is meant a compound capable of modifying, especially by increasing, the speed of the chemical reaction wherein it participates, and which is regenerated at the end of the reaction. This definition covers both catalysts, i.e. compounds that exercise their catalytic activity without needing to undergo any modification or conversion, and compounds (also called "pre-catalysts") which are introduced into the reaction medium and that are converted into a catalyst.

"Alkyl", for the purposes of the present invention, means a linear, branched or cyclic, saturated, optionally substituted carbon radical comprising 1 to 12 carbon atoms. The alkyl can comprise, for example, 1 to 8 carbon atoms, or again from 1 to 6 carbon atoms. For a saturated, linear or branched alkyl, mention can be made for example of methyl, ethyl, propyl, butyl, pentyl, hexyl, heptyl, octyl, nonyl, decyl, undecyl, dodecanyl radicals and the branched isomers thereof. As cyclic alkyl, mention can be made of cyclopropyl, cyclobutyl, cyclopentyl, cyclohexyl, bicylco[2,1,1] hexyl, bicyclo[2,2,1] heptyl radicals.

By "alkenyl" or "alkynyl" is meant an unsaturated linear carbon radical, branched or cyclic, optionally substituted, said unsaturated carbon radical comprising 2 to 12 carbon atoms comprising at least one double (alkenyl) or a triple bond (alkynyl). The alkenyl or alkynyl can comprise, for example, 2 to 8 carbon atoms, or again from 2 to 6 carbon atoms. As such, mention can be made, for example, of ethylenyl, propylenyl, butenyl, pentenyl, hexenyl, acetylenyl, propynyl, butynyl, pentynyl, hexynyl radicals and their branched isomers. As unsaturated cyclic alkenyls, mention can be made, for example, of cyclopentenyl, cyclohexenyl.

The alkyl, alkenyl and alkynyl group, for the purpose of the invention, can optionally be substituted by one or more hydroxyl groups; one or more alkoxy groups; one or more halogen atoms chosen from among the atoms of fluorine, chlorine, bromine and iodine; one or more nitro groups (—NO2); one or more polystyrene radicals; one or more nitrile groups (—ON); one or more aryl groups, with the alkoxy and aryl groups as defined in the scope of the present invention.

The term "aryl" designates in general a cyclic aromatic substituent comprising from 6 to 20 carbon atoms. The aryl can comprise, for example, from 6 to 10 carbon atoms. In the scope of the invention the aryl group can be mono- or polycyclic. As an indication, mention can be made of the phenyl, benzyl and naphtyl groups. The aryl group can optionally be substituted by one or more hydroxyl groups; one or more alkoxy groups; one or more halogen atoms chosen from among the atoms of fluorine, chlorine, bromine and iodine; one or more nitro groups (—NO2); one or more nitrile groups (—ON); one or more alkyl groups, one or more polystyrene radicals; with the alkoxy and alkyl groups as defined in the scope of the present invention.

The term "alkoxy" means an alkyl, alkenyl and alkynyl group, as defined above, linked by an oxygen atom (—O-alkyl, O-alkenyl, O-alkynyl).

By halogen atom is meant an atom chosen from among the atoms of fluorine, chlorine, bromine and iodine.

By additive, within the meaning of the invention, is meant a compound capable of improving the solubility and reactivity of the reagents for the conversion of the formates.

As indicated, in the method of the invention, alkyl formate has the formula (I)

$$H\text{—COOR} \qquad (I)$$

wherein R is an alkyl comprising 1 to 12 carbon atoms, said alkyl optionally being capable of being substituted by a substituent as defined above.

According to a first embodiment of the invention, R is an alkyl comprising 1 to 8 carbon atoms, said alkyl can optionally be substituted by a substituent as defined above. In this embodiment, R is methyl, ethyl, propyl, butyl, pentyl, hexyl, heptyl, octyl. Preferably, R is methyl, ethyl, propyl and n-butyl.

The method of the invention uses a catalyst forming part of the family of strong bases, i.e. a catalyst which can be an alcoholate having a pKa>15 in water; or pKa>27 in acetonitrile or DMSO or a nitrogenous base having a pKa>15 in water; or a pKa>27 in acetonitrile or DMSO.

According to a second embodiment of the invention, the catalyst is an alcoholate of formula (II)

$$R'\text{—O-M} \qquad (II)$$

wherein
R' is an alkyl comprising 1 to 6 carbon atoms, an alkenyl comprising 2 to 6 carbon atoms, an alkynyl comprising 2 to 6 carbon atoms, or an aryl comprising 6 to 10 carbon atoms; and
M is an alkali metal chosen from among Li, Na, K, Cs or Rb; or
M is a quaternary ammonium of formula (III)

wherein

R$_1$, R$_2$, R$_3$, R$_4$ and R$_5$ represent, independently one from the other, a hydrogen atom, an alkyl comprising 1 to 6 carbon atoms, an aryl comprising 6 to 10 carbon atoms, said alkyl and aryl being optionally substituted.

In this second embodiment, preferably R' is an alkyl comprising 1 to 6 carbon atoms. The alkyl can be chosen from among methyl, ethyl, propyl, butyl, pentyl or hexyl.

In this second embodiment, when M represents an alkali metal, said alkali metal is preferably Li, Na, K or Rb.

Still in this second embodiment, the alcoholate is chosen from among CH$_3$—OLi, CH$_3$—ONa, CH$_3$—OK, CH$_3$—ORb, CH$_3$CH$_2$—OK, or tBu-OK.

When M is a quaternary ammonium of formula (III), preferably R$_2$, R$_3$, R$_4$ and R$_5$ represent, independently one from the other, a hydrogen atom, an alkyl comprising 1 to 6 carbon atoms, an aryl comprising 6 to 10 carbon atoms, said aryl being optionally substituted in particular by one or more polystyrene radical(s).

The catalysts of formula (II), wherein M is a quaternary ammonium of formula (III), can optionally be supported. The active phase is then grafted onto a support, e.g. a polymer support.

When M is a quaternary ammonium of formula (III), said quaternary ammonium is preferably, (C$_6$H$_5$CH$_2$)(CH$_3$)$_3$N$^+$, or polystyrene-(C$_6$H$_4$CH$_2$)(CH$_3$)$_3$N$^+$, the latter being the supported form of benzyletrimethylammonium.

Still in this embodiment, when M is a quaternary ammonium the alcoholate is chosen from among CH$_3$—O$^-$ (C$_6$H$_5$CH$_2$)(CH$_3$)$_3$N$^+$, or CH$_3$—O$^-$ polystyrene-(C$_6$H$_4$CH$_2$)(CH$_3$)$_3$N$^+$, the latter being the supported form of benzyl trimethylammonium methanolate.

Figure 3:
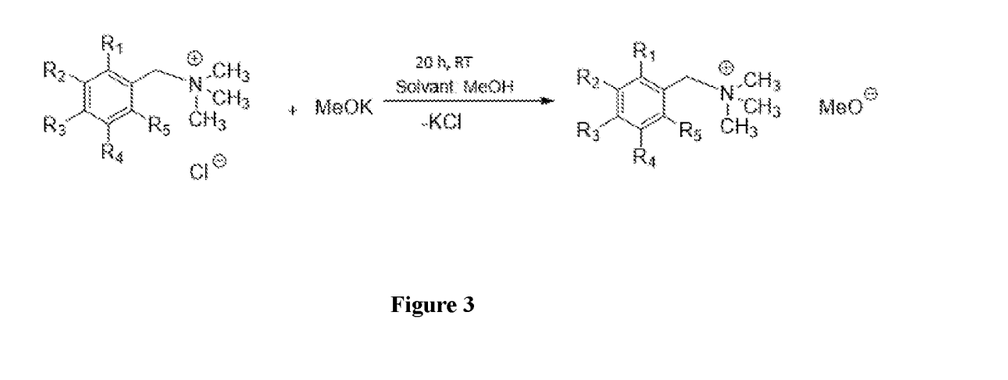
FIG. 3 represents the reaction enabling the preparation of the methanolates of benzyltrimethylammonium $CH_3$—$O^-$ $(C_6H_5CH_2)(CH_3)_3N^+$ according to the procedure described in Org. Synth. 1958, 38, 5 DOI: 10.15227/orgsyn.038.0005.

The above-mentioned benzyltrimethylammonium methanolate can be prepared according to the procedure described in Org. Synth. 1958, 38, 5 DOI: 10.15227/orgsyn.038.0005 according to the reaction of FIG. 3.

Figure 4:
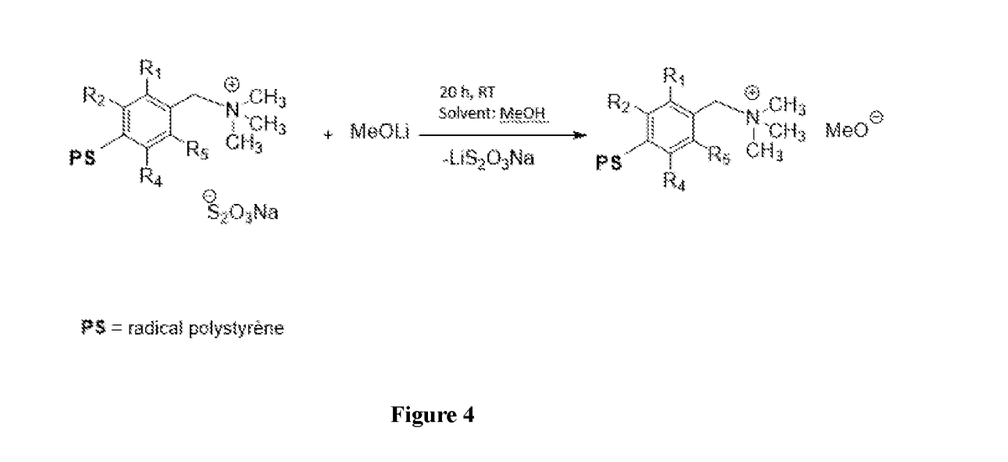
FIG. 4 represents the reaction enabling the preparation of the supported version of the methanolates of benzyltrimethylammonium, in particular $CH_3$—$O^-$ $(C_6H_4CH_2)(CH_3)_3N^+$ according to the procedure described in Org. Synth. 1958, 38, 5 DOI: 10.15227/orgsyn.038.0005.

The supported version of benzyltrimethylammonium methanolates, especially CH$_3$—O$^-$ polystyrene-(C$_6$H$_5$CH$_2$)(CH$_3$)$_3$N$^+$ can also be prepared according to the procedure described in *Org. Synth.* 1958, 38, 5 DOI: 10.15227/orgsyn.038.0005. In the case of the supported ammoniums, advantageously the commercial product is used wherein the polymer is already grafted with the ammonium.

According to a third embodiment of the invention, the catalyst is a nitrogenous base having a pKa>15 in water; or a pKa>27 in acetonitrile or DMSO. In this embodiment, the catalyst is, preferably, a alkaline bicyclic guanidinate chosen from among the bicyclic guanidinates of sodium or potassium, especially sodium or potassium salts of 1,3,4,6,7,8-hexahydro-2H-pyrimido[1,2-a]pyrimidine (or Hhpp) anion; or an alkaline amide substituted by alkyls comprising 1 to 6 carbon atoms, especially lithium, sodium or potassium salts of dimethylamide, diethylamide, or diisopropylamide.

The method of the invention, can use, in addition, at least one additive. The additive, whose role is to improve the solubility and the reactivity of the reagents for the conversion of the formates, can be chosen, for example, from among crown ethers chosen from among 12-crown-4, 15-crown-5, 18-crown-6, dibenzo-18-crown-6, benzo-18-crown-6, benzo-15-crown-5, or dibenzo-15-crown-5, aza-crowns chosen from among 1,4,7,10-tetraazacyclododecane (cyclen), 1,4,7,10,13,16-hexaazacyclooctadecane (hexacyclen), or diaza-18-crown-6, crown thioethers chosen from among 1,5,9,13-tetrathiacyclohexadecane (16-Ane-S4), or 1,4,7,10,13,16-hexathiacyclooctadecane (18-Ane-S6), or cryptands chosen from among [2,1,1], [2,2,1], [2,2,2], [2,2,2]B, [2,2,3], [2,3,3], [3,3,3].

The production of carbon monoxide (CO) using an alkyl formate of formula (I), takes place in a or a mixture of at least two polar and aprotic solvents. This solvent is preferably chosen from among ethers chosen from among diethylic ether or tetrahydrofurane (THF);

nitrogenous solvents chosen from among N,N-dimethylformamide (DMF), pyridine, N-methyl-2-pyrrolidone or 1-methyl-2-pyrrolidone (NMP);

ketones chosen from among acetone or butan-2-one; or sulphoxides such as dimethylsulphoxide (DMSO).

The temperature of the production of carbon monoxide (CO) according to the method of the invention wherein an alkyl formate of formula (I) is used, is less than or equal to 30° C. Preferably the temperature is comprised between 10 and 30, more preferably between 15 and 30° C., inclusive.

In the method of the invention, the conversion of the alkyl formate of formula (I) into CO, generates a gas pressure resulting from the formation of carbon monoxide. The reaction can then occur under pressure of carbon monoxide (closed system), or under atmospheric pressure (1 bar or 10$^5$ Pa) of inert gases (N$_2$ and/or argon), for example, in a burette (open system). The production of carbon monoxide (CO) making use of an alkyl formate, takes place, preferably, in an inert atmosphere under pressure of dinitrogen (N$_2$), argon or a mixture of these gases.

The reaction time depends on the rate of conversion of the alkyl formate of formula (I). Advantageously the reaction is maintained to the complete conversion of the alkyl formate into CO. The reaction time can be 1 minute to 200 hours, preferably 5 minutes to 48 hours, more preferably 15 minutes to 4 hours, inclusive.

The amount of catalyst used in the method of the invention is from 0.1 to 10 mol %, preferably from 2 to 5 mol %, inclusive, compared to the alkyl formate of formula (I).

When an additive is used, the amount of additive is from 0.1 to 10 mol %, preferably from 2 to 5 mol %, inclusive, compared to the alkyl formate of formula (I).

The CO produced by the method of the invention can be used as it is or be purified. Traces of solvents, of alkyl formate or alcohol formed can be eliminated by condensation, leading to pure CO. When the CO produced is isolated, the production yield of CO can reach 100% {% yield=amount of CO obtained (moles)/amount of starter alkyl formate (moles)×100}.

The various reagents used directly or indirectly in the method of the invention in particular, formic acid, alkyl formates, (pre)catalysts, additives, and solvents are, in general, commercial compounds/solvents or can be prepared by the methods already described in the literature and known to the skilled person in the art.

Alkyl formate of formula (I) can be obtained by esterification of formic acid with an alcohol of formula ROH wherein R is alkyl comprising 1 to 12 carbon atoms, in order to obtain the corresponding formate, for example by simple distillation. Distillation is possible and efficient so long as there are no azeotropes between reagents, products and solvent and that the following inequations on the boiling temperatures are satisfied:

$$T_{b(formate)} < T_{b(alcohol)}$$

$$T_{b(formate)} < T_{b(formic\ acid)}.$$

Formic acid, in turn, can be obtained by the traditional industrial method, by hydrogenation or by electro-reduction at 2e⁻ of $CO_2$ (step (i)). The formation of formic acid can advantageously be done by reduction at 2e⁻ of $CO_2$, preferably carried out according to the most selective and effective methods know to date. For example, catalytic hydrogenation of $CO_2$ can be carried out according to the protocol of Laurenczy et al. (S. Moret, P. J. Dyson, G. Laurenczy, *Nat. Commun.*, 2014, 5, 1-7), making it possible to recover up to 1.9 M of formic acid in DMSO. Regarding the electro-reduction at 2e⁻ of $CO_2$, this can be carried out, for example, according to the conditions of Shibata et al. (N. Furuya, T. Yamazaki, M. Shibata, *J. Electroanal. Chem.*, 1997, 431, 39-41) or of Hon et al. (Y. Hori, H. Wakebe, T. Tsukamoto, O. Koga, *Electrochim. Acta*, 1994, 39, 1833-1839)

It should be noted that the electro-reductions are dependent on a large number of parameters such as the nature of the reactor, the electrodes, the electrolyte or again the electro-catalyst used. These concepts and different systems making it possible to obtain formic acid are discussed in the reviews of Olah et al. (A. Goeppert, M. Czaun, J. P. Jones, G. K. Surya Prakash, G. A. Olah, *Chem. Soc. Rev.*, 2014, 43, 7995-8048), of Leung, Xuan et al. (X. Lu, D. Y. C. Leung, H. Wang, M. K. H. Leung, J. Xuan, *ChemElectroChem*, 2014, 1, 836-849) or again of Kenis et al. (H.—R. M. Jhong, S. Ma, P. J. A. Kenis, *Curr. Opin. Chem. Eng.*, 2013, 2, 191-199).

The formic acid thus formed in step (i) can then be used in the next step (ii) which is the preparation of alkyl formate of formula (I).

Step (ii) consists of putting into reaction:
the formic acid obtained in the first step, either directly in the same reaction medium or after having treated the catalyst by eliminating it or by separating it from the reaction medium or, by deactivating it in the reaction medium;
an alcohol (2 to 6 molar equivalents compared to the formic acid, preferably, 3 molar equivalents); and
by carrying out a continuous distillation, i.e. that the reaction medium is topped with a distilling device (preferably with a Vigreux column) and heated to a temperature enabling selective distillation of the target formate (e.g. between 62° C. and 80° C. for methyl formate):

The alkyl formate of formula (I) coming from step (ii) is then put into contact with a catalyst as defined above, in a solvent chosen from among those mentioned above, at a temperature less than or equal to 40° C. (step (iii)).

Figure 1:
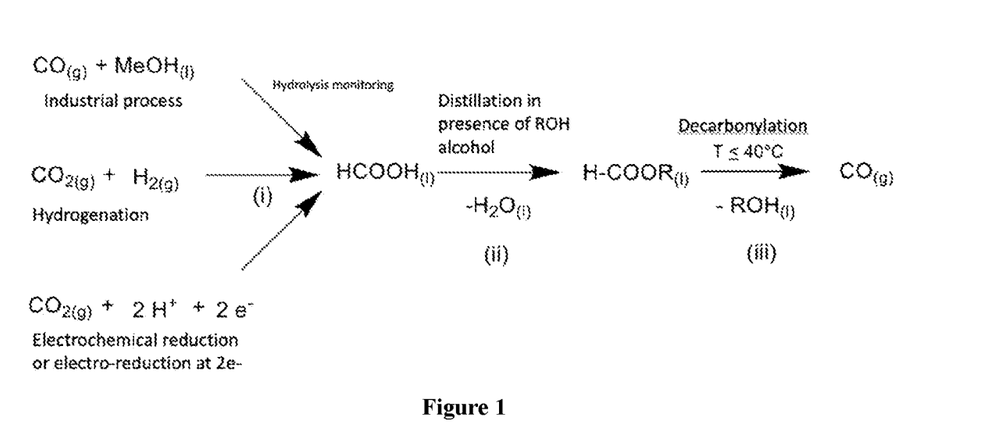
FIG. 1 represents steps (i) to (iii) leading to the production of carbonyl by the method of the invention.

FIG. 1 represents steps (i) to (iii) leading to the production of carbonyl by the method of the invention.

The operating conditions described in this document apply to all embodiments of the method of the invention.

Apart from the excellent economic viability of the method of the invention compared to the methods of the state of the art described, it has the following advantages.

The formic acid and the alkyl formate are liquid in normal conditions of temperature and pressure (18 to 25° C. and pressure 1 bar or $10^5$ Pa), which makes it easy to transport with lower costs and risks than the transportation of gas such as hydrogen. This is particularly useful when production of the formic acid and the decarbonylation of the alkyl formate is carried out in two separate places.

Formic acid is non-toxic in dilute solution (concentration less than 85% mass in water) and is thus a benign reagent.

Most of the alkyl formates (e.g. methyl or ethyl formate) are non-toxic and can thus be considered benign reagents.

In the method of the invention, CO production is catalyzed with a catalyst comprising an abundant alkali metal, unlike catalysts of the state of the art which make use of metals that are scarce, of high cost and problematic toxicity.

The catalysts used are commercial, or easily prepared by the skilled person in the art from inexpensive commercial reagents. In contrast, when metals such as those of the state of the art are used, the ligands used to stabilise them are expensive and their preparation most often requires multiple synthesis steps.

Additionally, if the formic acid is obtained by the catalytic hydrogenation of $CO_2$, this conversion uses solvents with boiling points much higher than the boiling temperature of the alkyl formates and especially of methyl formate.

Thus there is compatibility between the steps (i) and (ii) described above when catalytic hydrogenation is chosen as the process of reduction of $CO_2$, and these two reactions can thus be carried out in sequence when the solvent used in step (i) is compatible with step (ii).

If electro-reduction of $CO_2$ is used, in most cases the medium used is aqueous which also turns out to be compatible with step (ii).

As long as there are no azeotropes between reagents, product and solvent, distillation is an efficient method for purifying alkyl formate. For example, in the case of methyl formate, there is no azeotrope in particular between methyl formate, water and methanol. Distillation makes it possible to obtain anhydrous methyl formate (possibly with 0 to 15% mole in MeOH as impurity). Impurity can be characterized by quantitative $^1$H NMR analysis.

The method of the invention can be used in all the industrial processes and at laboratory scale requiring pure carbon monoxide.

Another object of the invention relates to a method chosen from among
the method of production of methanol,
the method of production of acetic acid (Monsanto method),
the method of olefin hydroformylation (oxo and aldox method),
the method of production of hydrocarbons (Fischer-Tropsch method), or
the method of nickel carbonylation (Mond method),
comprising a step of production of carbon monoxide using an alkyl formate of formula (I) by the method according to the invention.

Figure 2:
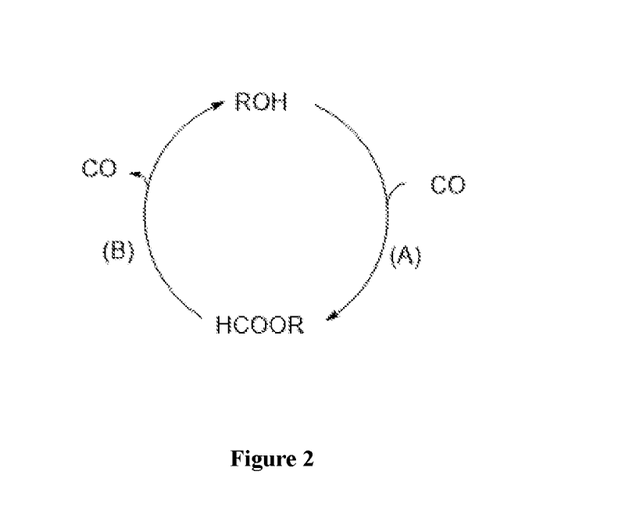
FIG. 2 represents the "CO pump" or "CO liquid storage" method comprising a step of production of carbon monoxide using an alkyl formate of formula (I) according to the method of the invention.

Another object of the invention concerns a "CO pump" or "CO liquid storage" method comprising a step of production of carbon monoxide using an alkyl formate of formula (I) according to the method of the invention as shown in FIG. 2. More particularly, the "CO pump" or "CO liquid storage" method is characterized in that it comprises
a first step (A) of formation of an alkyl formate of formula (I) by carbonylation of an alcohol of formula ROH, with R representing an alkyl comprising 1 to 12 carbon atoms, preferably a methyl, and
a second step (B) of production of carbon monoxide using an alkyl formate of formula (I) by the method according to the invention.

In the step (A), the formation of an alkyl formate of formula (I) by carbonylation of an alcohol of formula ROH, with R representing an alkyl comprising 1 to 12 carbon atoms, preferably a methyl, can be carried out according to the industrial process described in U.S. Pat. No. 4,216,339.

Other advantages and characteristics of the present invention will appear on reading the following examples given for illustrative purposes and not limiting and the appended figures.

EXAMPLES

In the examples, carbon monoxide was characterized by:
$^{13}C$ NMR: Bruker DPX 200 MHz spectrometer
IR: IRAffinity 15 Shimadzu and gas analysis cell
GC: GC-2010 Plus Gas chromatograph Shimadzu
$^1H$ NMR: Bruker DPX 200 MHz spectrometer.

The reagents, catalysts, additives, solvents used are either commercial or prepared according to the indicated reference:

Water: Water Millipore Milli-Q Gradient
DMSO: Carlo Erba 1 L Pure for synthesis
DCM: Carlo Erba 1 L Pure for synthesis
Methanol: Carlo Erba 1 L Anhydrous for analysis
Methyl formate: Acros organics 500 mL 97% CAS: 107-31-3
Ethyl formate: Merck 100 mL Ref: 800891 CAS: 109-94-4
nButyl formate: Alfa Aesar 50 mL Ref: A13882 CAS: 592-84-7
MeOK: Sigma Aldrich 5G 95% CAS: 865-33-8
MeONa: Sigma Aldrich 100G 95% CAS: 124-41-4
MeOLi: Sigma Aldrich 98% Ref: 344370-25G CAS: 865-34-9
EtOK: Sigma Aldrich 100G CAS: 917-58-8
tBuOK: Sigma Aldrich 100G CAS: 865-47-4
MeORb: Preparation according to the method described by S. I. Drakin, R. K. Kurmalieva, M. K. Karapet'yants, Teoreticheskaya i Eksperimental'naya Khimiya, 1966, Vol 2, pages 40-44
Khpp: Preparation according to: M. P. Coles, P. B. Hitchcock, Aust. J. Chem., 2013, 66, 1124-1130.
Nahpp: Preparation according to: A. A. Mohamed, A. P. Mayer, H. E. Abdou, M. D. Irwin, L. M. Pérez, J. P. Fackler, Inorg. Chem., 2007, 46, 11165-11172.
Khpp: Preparation according to: M. P. Coles, P. B. Hitchcock, Aust. J. Chem., 2013, 66, 1124-1130.
12C4 (12-crown-4 or 1,4,7,10-tetraoxacyclododecane): Fluka 5 mL CAS: 294-93-9
18C6 (18-crown-6 or 1,4,7,10,13,16-hexaoxacyclooctadecane): Sigma Aldrich ≥99% 1 G CAS: 17455-13-9
DMF: Sigma Aldrich 99.8% 1 L CAS: 68-12-2
Benzyltrimethyl ammonium chloride: Sigma Aldrich 99% CAS: 56-37-1
polystyrene-$(C_6H_4CH_2)(CH_3)_3N^+S_2O_3Na^-$: Thiosulfate, polymer-bound reference sigma aldrich 589977

Preparation of an Alkyl Formate of Formula (I)

The preparation of alkyl formate by distillation can be carried out according to the following experimental protocol:

1. In air, in a distillation flask introduce pure formic acid as well as water or DMSO (according to the method for obtaining formic acid), or formic acid recovered with its reaction medium by the above-mentioned methods.
2. Add alcohol (2 to 6 molar equivalents in respect to the formic acid, preferably, 3 molar equivalents).
3. Top this with a distillation device (preferably with a Vigreux column) equipped with an outlet trap at a low temperature (from 0° C. to −30° C., preferably −20° C.).
4. The flask is then heated to a temperature chosen according to the formate to enable continuous distillation specific to the formate.
5. The reaction is ended when there is no more alkyl formate condensing.

The table below presents some of the results obtained in the case of methyl formate:

| Formic acid | MeOH (13.8 mL, 318 mmol) | Solvent | Yield in isolated methyl formate (%) |
|---|---|---|---|
| 4 mL, 106 mmol | 13.8 mL, 318 mmol | Water | 86% Impurity: 9% MeOH |
| 4 mL, 106 mmol | 13.8 mL, 318 mmol | DMSO | 71% Impurity: 13% MeOH |

In this table, the calculated yield is the ratio of the number of moles of methyl formate recovered compared to the number of moles of formic acid introduced corrected by the purity observed by $^1H$ NMR analysis.

Method of Production of Carbon Monoxide (CO) Making Use of an Alkyl Formate of Formula (I) According to the Invention in Closed System 1. Under inert atmosphere, in glove box, the catalyst, alkyl formate, solvent, and optionally an additive are introduced in a Schlenk tube which is then sealed by a J. Young tap. The order of introduction of the reagents requires putting in the catalyst or the formate last.
2. The Schlenk tube is then agitated at a temperature between 15 and 30° C.

The table below presents some of the results obtained with DMF as solvent:

| Reagent (1 mmol) | Catalyst (5 mol %) | Conversion (%)[a] |
|---|---|---|
| None | None | No CO detected |
| None | MeOK | No CO detected |
| H—COOMe | None | 0% |
| H—COOMe | MeOLi/12C4 | 12% in 3 h at RT |
| H—COOMe | MeOLi | 54% in 8 h at 30° C. |
| H—COOMe | MeONa/18C6 | 56% in 3 h at RT |
| H—COOMe | MeONa | 46% in 3 h at 30° C. |
| H—COOMe | MeONa (1.5 mol %) | 49% in 3 h at 30° C. |
| H—COOMe | MeOK | 50% in 4 h at RT |
| H—COOMe | MeORb | 44% in 3 h at RT |
| H—COOMe | EtOK | 44% in 1 h at RT |
| H—COOMe | tBuOK/18C6 | 60% in 3 h at RT |
| H—COOMe | tBuOK | 59% in 3 h at 30° C. |

-continued

| Reagent (1 mmol) | Catalyst (5 mol %) | Conversion (%)[a] |
|---|---|---|
| H—COOMe | Khpp | 50% in 4 h at RT |
| H—COOMe | Nahpp/18C6 | 49% in 3 h at RT |
| H—COOMe | Nahpp | 56% in 3 h at 30° C. |
| H—COOEt | MeOK | 77% in 2 h3 0 min at RT |
| H—COOEt | EtOK | 51% in 1 h at RT |
| H—COOn—Bu | tBuOK/18C6 | 40% in 3 h at RT |
| H—COOn—Bu | tBuOK | 60% in 3 h at 30° C. |

Solvent used: DMF (600 µL).
[a]The percentage of conversion is calculated by $^1$H NMR analysis of the reaction crude, indirectly by integration of the signal of the alcohol formed at the same time as the CO, compared to the alkyl formate introduced.
RT: around 19° C.
KHpp: the potassium salt of anion of 1,3,4,6,7,8-hexahydro-2H-pyrimido[1,2-a] pyrimidine.
NaHpp: the sodium salt of anion of 1,3,4,6,7,8-hexahydro-2H-pyrimido[1,2-a] pyrimidine.

| Reagent (1 mmol) | Catalyst (5 mol %) | Solvent | Conversion (%)[a] |
|---|---|---|---|
| H—COOMe | MeOK | DMF | 50% in 3 h at RT |
| H—COOMe | MeOK | NMP | 50% in 3 h at RT |
| H—COOMe | MeOK | THF | 14% in 3 h at RT |
| H—COOMe | MeOK | Et$_2$O | 10% in 3 h at RT |
| H—COOMe | MeOK | DCM | 0% in 3 h at RT |

[a]The percentage of conversion is calculated by $^1$H NMR analysis of the reaction crude, indirectly by integration of the signal of the alcohol formed at the same time as the CO, compared to the alkyl formate introduced.
RT: around 19° C.

Method of Production of Carbon Monoxide (CO) Making Use of Methyl Formate According to the Invention in Open System
1. Under inert atmosphere, with a single inlet of argon or dinitrogen, the catalyst, solvent, optionally an additive are introduced in a reaction flask equipped with a pressure-equalizing dropping funnel. The order of introduction of the reagents is not important.
2. The methyl formate and the solvent are introduced into the dropping funnel.
3. The argon or dinitrogen inlet is closed.
4. The formate is added.
5. The flask is then agitated at ambient temperature (around 19° C.) by recovering the carbon monoxide by a third neck.

The table below presents some of the results obtained with methyl formate, CH$_3$OK as catalyst and DMF as solvent:

| H—COOMe | CH$_3$OK | DMF (ml) | Yield (%)[a] |
|---|---|---|---|
| 1 mmol | 5 mol % | 17.5 | 74% in 14 min 6 s at 19° C. |
| 1 mmol | 5 mol % | 20.4 | 86% in 2 h 20 min at 19° C. |
| 1 mmol | 6 mol % | 17.5 | 74% in 11 min 45 s at 19° C. |
| 1 mmol | 7 mol % | 17.5 | 74% in 8 min 16 s at 19° C. |
| 1 mmol | 8 mol % | 17.5 | 74% in 8 min 4 s at 19° C. |
| 1 mmol | 8 mol % | 17.5 | 74% in 8 min 2 s at 19° C. |

[a]The yield is calculated by the ratio of n = number of moles of CO recovered (proportional to the volume observed assuming the ideal gas law PV = nRT using P = atmospheric pressure 1013.25 hPa, T = laboratory temperature 19° C., R = ideal gas constant, V = volume of CO observed) to the number of moles of methyl formate used.

Method of Preparation of Methanolates of Benzylmethylammonium CH$_3$—O$^-$ (C$_6$H$_5$CH$_2$)(CH$_3$)$_3$N$^+$ and CH$_3$—O$^-$ Polystyrene-(C$_6$H$_4$CH$_2$)(CH$_3$)$_3$N$^+$ These catalysts are prepared according to the procedure described in *Org. Synth.* 1958, 38, 5 DOI: 10.15227/orgsyn.038.0005.

Method of Production of Carbon Monoxide (CO) Making Use of an Alkyl Formate of Formula (I) According to the Invention in Closed System
1. Under inert atmosphere, in glove box, the catalyst, alkyl formate, solvent, and optionally an additive are introduced in a Schlenk tube which is then sealed by a J. Young tap. The order of introduction of the reagents requires putting in the catalyst or the formate last.
2. The Schlenk tube is then agitated at a temperature between 15 and 30° C.

The table below presents some of the results obtained with DMF as solvent:

| Reagent (1 mmol) | Catalyst (5 mol %) | Conversion (%)[a] |
|---|---|---|
| H—COOMe | CH$_3$—O$^-$(C$_6$H$_5$CH$_2$)(CH$_3$)$_3$N$^+$ | 58% in 3 h at RT |
| H—COOMe | CH$_3$—O$^-$PS—(C$_6$H$_4$CH$_2$)(CH$_3$)$_3$N$^+$ | 37% in 3 h at RT |

Solvent used: DMF (600 µL).
[a]The percentage of conversion is calculated by 1 H NMR analysis of the reaction crude, indirectly by integration of the signal of the alcohol formed at the same time as the CO, compared to the alkyl formate introduced.
RT: around 19° C.
PS: polystyrene radical

The invention claimed is:
1. A method of production of carbon monoxide (CO) wherein an alkyl formate of formula (I)

$$H-COOR \quad (I)$$

where R is an alkyl comprising 1 to 12 carbon atoms, is put into contact with a catalyst, said method being characterized in that the catalyst is chosen from among:
an alcoholate of formula (II)

$$R'-O-M \quad (II)$$

wherein
R' is an alkyl comprising 1 to 6 carbon atoms, an alkenyl comprising 2 to 6 carbon atoms, an alkynyl comprising 2 to 6 carbon atoms, or an aryl comprising 6 to 10 atoms; and
M is an alkali metal selected from among Li, Na, K, Cs or Rb; or
M is a quaternary ammonium of formula (III)

wherein
R$_1$, R$_2$, R$_3$, R$_4$ and R$_5$ represent, independently one from the other, a hydrogen atom, an alkyl comprising 1 to 6 carbon atoms, an aryl comprising 6 to 10 carbon atoms, said alkyl and aryl being optionally substituted; or
a nitrogenous organic base selected from among the alkaline bicyclic guanidinates selected from among the bicyclic guanidinates of sodium or potassium; or an alkaline amide substituted by alkyls comprising 1 to 6 carbon atoms; and in that the putting into contact is carried out in a or in a mixture of at least two polar and aprotic solvents selected from among:
ethers selected from among diethylic ether or tetrahydrofurane (THF);
nitrogenous solvents selected from among N,N-dimethylformamide (DMF), pyridine, N-methyl-2-pyrrolidone or 1-methyl-2-pyrrolidone (NMP);
ketones selected from among acetone or butan-2-one; or
dimethylsulphoxide (DMSO),
at a temperature less than 35° C.

2. The method according to claim 1, characterized in that the alcoholate of formula (II)

wherein
R' is an alkyl comprising 1 to 6 carbon atoms; and
M is an alkali metal selected from among Li, Na, K, or Rb.

3. The method according to claim 1, characterized in that the alcoholate of formula (II) is selected from among $CH_3$—OLi, $CH_3$—ONa, $CH_3$—OK, $CH_3$—ORb, $CH_3CH_2$—OK, or tBu-OK.

4. The method according to claim 1, characterized in that the alcoholate of formula (II)

wherein
R' is an alkyl comprising 1 to 6 carbon atoms; and
M is a quaternary ammonium of formula (III)

wherein
$R_1$, $R_2$, $R_3$, $R_4$ and $R_5$ represent, independently one from the other, a hydrogen atom, an alkyl comprising 1 to 6 carbon atoms, an aryl comprising 6 to 10 carbon atoms, said alkyl and aryl being optionally substituted by one or more polystyrene radical(s).

5. The method according to claim 1, characterized in that the alcoholate of formula (II) is selected from among $CH_3$—O⁻$(C_6H_5CH_2)(CH_3)_3N^+$, or $CH_3$—O⁻(polystyrene-$C_6H_4CH_2)(CH_3)_3N^+$.

6. The method according to claim 1, using, in addition, at least one additive selected from among
crown ethers selected from among 12-crown-4, 15-crown-5, 18-crown-6, dibenzo-18-crown-6, benzo-18-crown-6, benzo-15-crown-5, or dibenzo-15-crown-5;
aza-crowns selected from among 1,4,7, 10-tetraazacyclododecane (cyclen), 1,4,7, 10,13,16-hexaazacyclooctadecane (hexacyclen), or diaza-18-crown-6;
crown thioethers selected from among 1,5,9,13-tetrathiacyclohexadecane (16-Ane-$S_4$), or 1,4,7,10,13,16-hexathiacyclooctadecane (18-Ane-S6); or
cryptands selected from among [2,1,1], [2,2,1], [2,2,2], [2,2,2]B, [2,2,3], [2,3,3], [3,3,3].

7. The method according to claim 1, characterized in that the temperature for bringing the alkyl formate of formula (I) into contact with the catalyst is less than or equal to 30° C.

8. The method according to claim 1, characterized in that production of carbon monoxide (CO) using an alkyl formate, takes place in an inert atmosphere under pressure of dinitrogen ($N_2$), argon or a mixture of these gases.

9. The method according to claim 1, characterized in that the amount of catalyst is from 0.1 to 10 mol %, inclusive, compared to the alkyl formate of formula (I).

10. The method according to claim 1, characterized in that the amount of additive used is from 0.1 to 10 mol %, inclusive, compared to the alkyl formate of formula (I).

11. The method according to claim 1, characterized in that the alkyl formate of formula (I) is obtained from formic acid by esterification of the formic acid with an alcohol of formula ROH wherein R is alkyl comprising 1 to 12 carbon atoms.

12. A method selected from among
the method of production of methanol,
the method of production of acetic acid (Monsanto method),
the method of olefin hydroformylation (oxo and aldox method),
the method of production of hydrocarbons (Fischer-Tropsch method), or
the method of nickel carbonylation (Mond method),
comprising a step of production of carbon monoxide using an alkyl formate of formula (I) by a method according to claim 1.

13. The method according to claim 1, characterized in that the catalyst is a nitrogenous organic base selected from among from among sodium or potassium salts of 1,3,4,6,7,8-hexahydro-2H-pyrimido[1,2-a]pyrimidine (or Hhpp) anion; or lithium, sodium or potassium salts of dimethylamide, diethylamide, or diisopropylamide.

14. The method according to claim 1, characterized in that the temperature for bringing the alkyl formate of formula (I) into contact with the catalyst between 10 and 30° C., inclusive.

15. The method according to claim 1, characterized in that the temperature for bringing the alkyl formate of formula (I) into contact with the catalyst is between 15 and 30° C., inclusive.

16. The method according to claim 1, characterized in that the amount of catalyst is from 2 to 5 mol %, inclusive, compared to the alkyl formate of formula (I).

17. The method according to claim 1, characterized in that the amount of additive used is from 2 to 5 mol %, inclusive, compared to the alkyl formate of formula (I).

* * * * *